US006130365A

United States Patent [19]
Peterson

[11] Patent Number: 6,130,365
[45] Date of Patent: Oct. 10, 2000

[54] BREEDING LINES OF COLOR-SEXABLE DAY-OLD CHICKS AND METHODS FOR PRODUCING THE SAME

[75] Inventor: Lloyd E. Peterson, Decatur, Ark.

[73] Assignee: Peterson Farms, Decatur, Ark.

[21] Appl. No.: 09/422,190

[22] Filed: Oct. 22, 1999

Related U.S. Application Data

[63] Continuation-in-part of application No. 09/127,899, Aug. 3, 1998, abandoned.

[51] Int. Cl.[7] .......................... A01K 37/00; A01K 67/00; B07C 5/00

[52] U.S. Cl. ................................ 800/8; 119/713; 209/509

[58] Field of Search ................................ 800/8; 119/713; 209/509

*Primary Examiner*—Bruce R. Campell
*Attorney, Agent, or Firm*—Shlesinger, Arkwright & Garvey LLP

[57] ABSTRACT

This invention relates to a method of producing a novel male parent line and a female parent line of meat-type chickens that are complementary to each other genetically so that upon mating the males of the male parent line to the female of the female parent line, the day-old chicks may be auto-sexed by down color by unskilled labor. The male chicks will be yellow-white down color, and the female chicks will be of reddish or buff down color. They may be readily separated by sex at the hatchery, transported to different brooder houses, and grown out separately on differently formulated feeds by sex; and although the female chicks nay start with some red feathers, these feathers will “fade out” in color and become white at broiler age. The male chicks start out with white feathers and retain white feathers at broiler age. Thus, all broilers are marketed with white feathers, eliminating any possibility for dark pin feathers on the dressed, eviscerated carcasses. This breeding model allows the option of mating the females of the female parent line with males of any orthodox commercial male parent line to produce unsexed day-old chicks, all with white-yellow down and subsequently all white feathers as broilers should any organization, broiler producer, farmer or company not be concerned with auto-sexing and growing sexes separately.

11 Claims, No Drawings

BREEDING LINES OF COLOR-SEXABLE DAY-OLD CHICKS AND METHODS FOR PRODUCING THE SAME

CASE HISTORY

This application is a C.I.P. of application Ser. No. 09/127,899, filed on Aug. 3, 1998 abandoned.

GENERAL DESCRIPTION

This invention relates to a first line of male and female chickens inbred with a "fade-out" gene, in which said male chicks at day-old are white and said female chicks at day-old are colored and color sexable from said male chicks; and in which said female chicks of said first line at broiler stage have lost their coloration and have become white like the male chicks at broiler stage; and a second line of female chickens not having the "fade-out" gene and mateable with said first line of male chickens to produce day-old male and female chicks having the "fade-out" gene; with said produced male day-old chicks being white and said female day-old chicks being colored and color-sexable.

HISTORICAL BACKGROUND

Before about the 1930's, nearly all farmers raised a few chickens, primarily for their own use for meat and eggs. Some farmers having a surplus of chickens, would sell them and their eggs locally. Some farmers, realizing that there was a market for chickens in the larger cities, began to sell live chickens at the farmer's markets. Those purchasing chickens would take them home and kill them, scald the carcasses to remove the feathers and eviscerate the carcasses. If the home owner did not want to handle the chickens, he or she could have the local butcher do the killing and processing. As demand for live chickens grew, some farmers began to specialize and begin trucking the live chickens such as Barred Plymouth Rocks into the cities in quantities. The poultry industry really started around 1932 and a large poultry house could handle about five hundred (500) chickens, but most farmers grew about two hundred and fifty (250) at a time. In the early days, it took about sixteen or seventeen weeks to get to a three pound average chicken. Today in seven weeks, we have achieved a four and a half pound (4½) chicken on average.

By the late 1930's, chicken was selling for fifty to sixty cents a pound live weight. This price is about the same today. At best, in the early years of chicken raising, a farmer could get only about three or four crops of chickens a year. Today, he averages about 6 to 7 crops. After World War II, the poultry industry took off and in the late 1950's, farmers built chicken houses for flocks of six or seven thousand. Most of the farmers who raised only smaller amounts eventually went out of the business. Today, most of the producers have between seven hundred fifty thousand to a million chickens per week year round.

Modern incubators can handle about eleven thousand eggs each an average size hatching can and produce about fifty-five thousand chicks a day allowing for losses. The supervised farms produce the eggs, which are bought back by the breeder who produces the chicks, which are sold back to the farmer along with required feed. When the chickens are five to seven weeks old, they go to a processing plant where they are cleaned, chilled or frozen, and shipped all over the United States to maintain the national tradition of chicken every Sunday.

In all of this development, it became necessary to develop eviscerating and processing equipment to handle the large numbers of broilers. The automatic equipment would de-feather and eviscerate the chickens and prepare the carcasses for packaging, freezing or refrigerating, depending upon the market demands as to whether the meat was to be fresh or frozen.

By 1960, eviscerated carcasses were being shipped by refrigerated trucks to markets (supermarket stores) and commercial market (restaurants) in large cities. They were displayed under glass in refrigerated cases in stores. Discriminating purchasers and housewives were able to detect any immature feathers, called "pin feathers" on the carcasses due to incomplete picking by mechanical pickers. If these "pin feathers" were red or black, then they were readily seen and portrayed as a dirty carcass. If the remaining "pin feathers" were white, they blended in with the natural skin color of the carcass and were not easily seen and for the most part, went undetected by the purchasers.

The processors quickly realized and acted on the advantages of a broiler with all white plumage, and in some instances abruptly ceased to accept red-feathered chickens for processing. Today, all commercial broilers are white plumaged; therefore, the orthodox method of auto-sexing chickens by mating red males to silver females to produce white males and red females broilers became unacceptable, because the red females would not be purchased by the processor and would have to be discarded as a total loss.

In essence, something had to be done to eliminate the loss problem. The resulting invention is designed to overcome the difficulties because it produces males with white plumage and bleaches out the red feathers of the females to become all white or at least with light red overcoating with white or creamy white undercoating of feathers with no detectable dark "pin feathers" portraying what appears to be a dirty carcass. In some instances, the males may have red feathering detectable as for instance on the back, neck or head, but dark "pin feathers" are notably absent.

Early sexing of the chicks was important, since the females could be housed separately without the need for feeding the chicks until they became of such size that the males could be easily distinguished from the females.

Broiler producers around the world have been searching for an efficient, economical method of determining the sex of day old chicks. Vent sexing and feather sexing have been used by the various broiler producers, but these methods have been found to have substantial economic disadvantages because of the substantial time required and labor costs in separating the male from the female chicks. The use of probes (Halverson et al. U.S. Pat. No. 5,508,165) is also an expensive procedure and not practical economically. Light sensing of anal areas of chicks (Suzuki U.S. Pat. No. 4,417,663) is another way of determining sex of chicks, but it is also expensive and time consuming as each chicks must be handled and manipulated. The use of experts who could feather sex the chicks has been used, but such experts are costly and feathering is time consuming.

This invention involves a unique observation. It was noticed that about 20% of broilers from a line designated as gold of commercial meat-type chickens, were white and 80% were reddish as expected. The 20% white broilers, "white sports," were separated out and grown under careful observation. They sprouted red feathers up to about 3 weeks of age, but as they grew older, the red color faded away due to fade out genes, and at broiler age of up to 7 weeks, they were practically white or at the least had a white undercoat of feathers.

Out of this observation, it was perceived that a process of producing broiler chickens through careful manipulation of the genetic composition of the male and female parent lines would increase the overall performance and efficiency of broiler production, thereby increasing profits to the poultry industry. The invention involves a continued production of broilers by mating a white feathered male parent line to a white feathered female line, resulting in broilers of both sexes with white feathers. As an additional option, the white female parent should be infused with the dominant so-called silver (S) gene, which is sex-linked, and if mated to a "fade-out" so called gold or red male, would at hatching produce white male day-old chicks and buff or reddish female chicks, thereby allowing separation of the sexes according to the down color. The above noted objections are overcome by infusing the genes of the "white sports" from the red male parent line into a fast growing, heavy-breasted current white parent male line and mating this new synthetic gold male line to the new white silver female line. This produces white feathered male broiler chicks at hatching, and distinctive buff or reddish female chicks at hatching, thus allowing auto-sexing by down color. These buff female chicks grow up to be acceptable broilers for processing and sale as clean carcasses to all final consumers because they inherit the "fade out" gene carried by the male parent and actually have white feathers or at least a white undercoat of feathers at broiler age and on processing will have no unsightly red "pin feathers."

OBJECTS AND SUMMARY OF THE INVENTION

An object of this invention is to synthesize a male line of chickens that will have the gold(s) plumage color genes together with the perceived major gene that causes juvenile red feathers to fade out to become white feathers at broiler age or at least to produce an undercoat of feathers that are white and not leave any unsightly red or dark colored "pin feathers" on the dressed broiler carcasses.

A further object of this invention is to synthesize a female line of chickens that will be pure for the sex-linked silver gene(S).

Another object of the this invention is to provide a mating between the two parent lines which will produce progeny that can be autosexed by down color at day of age, but during the development of the juvenile feathers, the red or buff color of the female broiler chick distinguishes the female from the white male at day of age, and will "fade out" to become white or at least produce a creamy white undercoat of feathers, so that none of the female broilers will have red or dark colored "pin feathers" on the dressed carcasses.

It is an object of this invention to provide chicks and a method for producing such chicks which are readily and easily colorsexed.

A further object of this invention is to provide chicks and a method for producing such chicks having distinctive male and female colors so that by hand, an unskilled person, or a simple photocell color sensing electronic apparatus in which the chicks are fed into a chute or similar device and pass a the photocell color sensor, which senses the overall color of the chicks as viewed from the position of the sensor automatically triggering a pusher, so that the chicks are selectively pushed to one side or the other of the chute into separate shipping container depending on whether the chicks are male white or female colored; can readily separate one day old male from one day old female chicks; thereby eliminating the need for specially trained and expensive observer personnel or expensive equipment.

Yet another object of this invention is to provide colorsexed chicks and a method for producing such colorsexed chicks so that each sex can be processed separately to a desired weight to reduce feed costs, since nutritional requirements for males and females are different. Females require less protein, calories, calcium and phosphorus. Males can be sent to the processing plant days earlier, and the separating provides a different environment for sexed chicks thereby stimulating a faster growth rate.

A further object of this invention is to provide color sexed chicks and a method for producing colorsexed chicks which permits the chicks of each sex to be substantially uniform in size and weight, with exceptional dressability, good fleshing, low condemnation and an above average percentage of Grade A broilers.

Still a further object of this invention is to provide separated flocks which are easier and more efficient to service and manage.

Another object of this invention is to eliminate the need for discarding female chicks, which heretofore were unacceptable to processors because of the tell-tale "pin feathers".

It is another object of this invention to produce a uniform size in the sexed chicks for processing by automatic equipment, which does not require constant adjustment due to variations in size thus keeping line interruptions at a minimum.

Yet a further object of this invention is to provide the consumer with a consistently higher quality of poultry.

Still another object of this invention is to provide a visual method for quickly colorsexing chicks which reduces labor costs in the processing.

A further object of this invention is to provide a method for colorsexing chicks, which is fast, reliable and constant in production.

A further object of this invention is to provide male and female lines of chicks, which can be mated to produce a commercial grade A broiler.

Another object of this invention is to provide a novel male parent line and a female parent line of meat-type chickens that are complementary to each other genetically, so that upon mating the males of the male parent line to the females of the female parent line, the day-old chicks may be autosexed by down color.

Yet another object of this invention is to produce a "non-fade-out" female line of chicks, which can be mated with male "fade-out" line to produce female "fade-out" chicks and also with a commercial grade of male white plumaged chicks.

In summary, this invention relates to the method of producing day old chicks whose sex can be readily distinguished by color for separation into male and female groups with the chicks having a "fade-out" gene so that the unsightly color normally found in color sexable female broilers will be unobservable due to the "fade-out" aspect.

Further, this invention is directed to the production of colorsexed chicks which can be readily colorsexed by unskilled labor or available overall color sensing photocell equipment, and which chicks are gender uniform in size and weight upon development into broiler size. These and other objects of this invention will be apparent from the following description and claims.

For general information purposes, the following may be helpful in understanding the gene nomenclature:

| | |
|---|---|
| I = | Dominant |
| II = | Homozygous dominant white. Prevents the expressions of black plumage |
| ii = | Homozygous recessive. Allows expression of black feathers |
| i = | Recessive gene to I dominant white |
| Ii = | Heterozygous for dominant white |
| CC = | Homozygous for full color expression on feathers |
| cc = | recessive white |
| Cc = | heterozygous for color expression |
| S = | sex linked Silver gene which obliterates red color |
| ss = | recessive to S for expression of red or gold in a male chick |
| S_ _ | recessive to S for expression of red or gold in a female chick |
| s(s) = | Recessive for expression of gold |
| e Locus = | A complex locus that determines the amount and distribution of red and black on the plumage of chickens (feathers) |
| ee = | Recessive from extended of black (E) resulting in extension of red or gold |
| $E^R$ = | birchen gene which produces a dark red color in the down and feathers |

References helpful in explaining the genetic nomenclature of poultry are:

a) Crawford, R D, 1990 "Poultry Breeding and Genetics, Chapters 5 and 6, 1st Edition, New York, El Sevier b) Somes, R. G. Jr., 1975, 1978, Registry of Poultry Genetic Stocks in North America, Storrs Agric. Exp. Sta. Bull, 437,446
References is also made to the following biography:
Lloyd Peterson and Peterson Industries
—An American Story—by Huey Crisp Published 1989 August Houser, Inc.

Little Rock, Ark.

Current

All commercial broilers are white plumaged; therefore, the orthodox method of auto-sexing chickens by mating red males to silver females to produce white male and red female broilers became unacceptable because the red females would not be purchased by processors and would have to be discarded as a total loss.

The novel genetic approach of this invention overcomes this difficulty enabling auto-sexing of day-old chicks by visual means by unskilled workers or by simple photocell color sensing inexpensive electronics sorting apparatus, because it produces males with white down and females with colored down and it bleaches out the red feathers of the females to become all white or at least light red overcoating with white or creamy white undercoating of feathers at broiler age.

The male and female genotype produced broiler genotype as follows:

| MALE LINE | | FEMALE LINE |
|---|---|---|
| II CC $E^R$ $E^R$ ss | X<br>↓ | ii cc ee S– |
| MALE BROILER OFFSPRING | | FEMALE BROILER OFFSPRING |
| Ii Cc $E^R$e Ss | | Ii CC $E^R$ e s– |
| White down color at day of age | | Buff or red down at day of age |

-continued

| | |
|---|---|
| White plumage as broilers | Fade-out white plumage or red over the tips with white undercoat feathers as broilers. No unsightly re "pin feathers" |

Therefore, the chronology of the development of this genetic package of breeding stocks that offers the option of auto-sexing is important.

DETAILED DESCRIPTION OF THE INVENTION

Since commercial broilers are to be produced, care must be taken to derive the required genes only from stocks with superior broiler performance, so that the resulting product will at the outset be commercially competitive and require the minimum selection to achieve acceptable performance in essential broiler performance traits such as growth rate, fleshing, conformation, fertility, hatchability, livability.

Accordingly, the initial stocks to be used are chosen by referencing performance of breeding stocks in industry available Random Sample Broiler tests conducted in the years 1950 through 1970, such as the Arkansas Random Sampling Broiler Tests and similar broiler random sampling tests conducted in other states in the U.S.A. and Canada. Any of the competitive modern commercial synthetic lines will also supply the background genetics for broiler performance.

Synthesize the Gold Male Parent Line

Step 1:

In order to have a high probability of assembling the required genes to synthesize a gold male line that has white plumage and that will transmit the gold genes along with the perceived "fade-out" gene and any associated beneficial modifying genes, the following breeds are pursued for available outstanding strains with superior broiler performance as determined by referencing:

Red Cornish (RC), Recessive White Cornish (RWC), and recessive white (as opposed to a dominant white) commercially available White Plymouth Rock (WPR), and, any modern commercial synthetic breeds developed from these standard breeds.

Males and females of the Red Cornish (RC), Recessive White Cornish (RWC) and White Plymouth Rock (WPR), selected for good meat-type fleshing and broiler performance, are intermingled and mass mated in floor pens.

Step 2:

At hatching, any chicks with black down, white down with black spots, chocolate to mahogany down, greenish down color, and in general any darkish-off-colors are culled or discarded.

Step 3:

Baby chicks that are yellowish white with any brownish or reddish spots on the head, neck and body are selected.

Step 4:

Identify the selected chicks with individual wing-bands, and record with a description of their down color.

Step 5:

These selected baby chicks are grown out on commercial broiler feed, so that their plumage color development can be observed, evaluated, and recorded as they grow to broiler age of 5 to 8 weeks old.

The main object is to secure several hundred chickens of good broiler quality that are white-tailed red (WTR) (red overcoat on the head, neck, hackle, and black and white tail feathers). Also, some chickens may be entirely of white plumage or predominantly white with occasional indiscriminate small patches of reddish feathers. These individuals will have a high probability of carrying the "fade-out" gene and they should also be retained for reproduction.

At maturity emphasis is placed on selecting males and females that conform with correct plumage color and with the body type of the modern broiler. Specifically individuals that have the appearance of white-tailed red (WTR) plumage pattern, genotype II CC ee s(s) are given special priority for selection to reproduce the lines as well as those that have faded out to white plumage, genotype II CC $E^R$ e s(s) or II CC $E^R$ $E^R$ s(s).

Step 6:

Each generation adult males and females that have fade-out plumage and plumage patterns that are close to white-tailed red (WTR) (red on head, neck, saddle, and back and thigh with white wing and tail feathers) will be chosen as breeders to reproduce the line. If this is done repeatedly, then the frequency of the individuals per generation that are white-tailed red (WTR) will greatly increase. Continue until homozygous, which can be determined by testing. About 10 generations will be sufficient to fix the line and make homozygous, (II CC s(s), and segregated for, $E^R$, and e, at the E locus). At this point of development the assurance of auto-sexing occurs, because mating these white-tailed red (WTR) and fade-out males to sex-linked silver females, cc ee S-, such as frequently found in white Wyandote and Sussex breeds, will produce yellow-white day old male chicks and buff or reddish day old female chicks.

The only further at this point is to eliminate the number of buff or reddish female day old chicks which will grow out with red juvenile feathers and be presented at the processing plant as fully red females. These red feathered females will produce dressed carcasses that have unsightly red "pin feathers" and be unacceptable to final consumers and housewives.

Step 7:

For this reason a further critical phase in refining the program becomes necessary. It must be determined which of the gold line males produce acceptable female broilers with little or no red plumage with a white undercoat of feathers. Indeed there will be some female broilers that will have had juvenile red feathers which faded out to become white feathers at broiler age, thereby avoiding any processed carcasses with unacceptable dark colored "pin feathers". The male parents that produces these fade-out female broilers will have carried the gene, ER, and associated modifying genes that accomplished the fading out of the red plumage in the female broilers.

In order to unmistakably identify these male parents that carry and transmit the fade-out genes, it becomes necessary to make individual male pedigree matings with silver females either by floor matings of one male to a number of females e.g. 10 females per pedigree pen or to artificially inseminate a number of females e.g. 10 females in cages per male.

Step 8:

Eggs are collected for 10 days and marked by male wing-band number, set together on trays. Then approximately on the 18th day of the incubation at transfer time the eggs from each sire mating are placed in pedigree baskets and transferred into hatchers.

Step 9:

Upon hatching, the individual baby chicks are wing-banded and the down color described in detail.

Step 10:

The chicks from all the sires are then intermingled and grown out as broilers. At broiler age the chickens are weighed individually, plumage colors and sex of chicken described and recorded by wing-band number.

Step 11:

Upon processing at the processing plant, the carcasses are examined for presence of any unsightly "pin feathers" and recorded wing-band number and attributed to the correct sire.

Step 12:

Upon summarizing the data, the sires that produce the most desirable female broilers of acceptable plumage color will be identified. These identified sires must be used to reproduce the next generation of the gold male parent line.

Step 13:

Repetition of this process for a minimum of five generations will establish a male parent line that carries the gold or red gene suitable for auto-sexing by mating to sex-linked silver females but will also carry the genes, $E^R$ $E^R$, and associated modifying fade-out genes that assure the auto-sexed day-old red females will produce essentially white plumage broilers acceptable in carcass quality to final consumers.

SUMMARY

| SYNTHESIS OF GOLD MALE PARENT LINE | |
|---|---|
| Red Cornish = | RC |
| White Plymouth Rock = | WPR |
| Recessive White Cornish = | RWC |
| White-Tailed Red = | WTR |
| Silver White Wyandote = | SWW |
| Sussex = | SX |

Step 1: RC×WC×WPR+any synthetic breeds developed from these standard breeds

↓

Step 2: Cull or discard any chicks with darkish-off color, e.g. black spots, chocolate or mahogany down, greenish down color.

↓

Step 3: Select baby chicks that are yellowish white with and brownish, or reddish spots on the head, neck and body.

↓

Step 4: Identify with wing bands and record with description and down color.

↓

Step 5: Grow to broiler age (5 to 8 weeks) and secure WTR+all white plumage+predominantly white with indiscriminate small patches of reddish feathers.

genotype II CC ee s(s)

genotype II CC $E^R$ e s(s)

genotype II CC $E^R$ $E^R$ s(s)

↓

Step 6: Repeat Step 5. To fix the line until auto-sexing results when at this point when males are mated with sex-linked silver females cc ee S- e.g. Silver White Wyandote (SWW) and Sussex (SX) breeds. Male chicks will be white and females chicks will be red or gold.

↓

Step 7: In order to unmistakably identify these male parents that carry and transmit the fade-out genes, it becomes necessary to make individual male pedigree matings with silver females either by floor matings of one male to a number of females e.g. 10 females per pedigree pen or to artificially inseminate a number of females e.g. 10 females in cages per male.

↓

Step 8: Collect eggs produced by the matings for about 10 days and mark by male wing numbers and set together on trays. On approximately the 18$^{th}$ day of incubation, the eggs are placed in pedigree baskets and transferred into hatchers.

↓

Step 9: Wing band the chicks at hatching and describe down color in detail.

↓

Step 10: Grow chicks to broiler age and weigh individually and check plumage color and sex of chicken, describe and record by wing band number.

↓

Step 11: Examine carcasses at processing plant and record presence of unsightly "pin feathers" by wing band number on correct sire.

↓

Step 12: Identify the sires producing the most desirable female broilers and use sires to produce next generation of the gold male parent line.

↓

Step 13: Repeat for about at least five generations to establish a male parent line that carries the gold or red gene for auto-sexing with sex-linked silver females, but will also carry the genes, $E^R$ $E^R$, and associated modifying fade-out genes that assure the auto-sexed day old red females will produce essentially white plumage accepted in carcass quality to customers.

To Synthesize a Sex-Linked Silver Female Parent Line

To establish a female parent line for producing auto-sexed broiler chicks, a female line pure for the sex-linked silver gene, S, must be established. For easy development and maintenance of such a line it is beneficial to have the background genotype of, ii, and cc. For accurate auto-sexing it is essential that the female parent be free of, E, the extended black allele.

There are various sources from which such a line may be synthesized. The White Wyandotte (SWW) and Sussex (SX) breeds are pure for sex linked silver.

The University of Arkansas and Brown's Ledbrest Breeding Company of Springdale, Ark., were well recognized sources of fast-feathering Wyandottes pure for the sex-linked silver gene. Also, Fischer Wyandotte from Canada was known to be pure for the silver gene. However, this strain was slow feathering.

In addition to these sources, some white Plymouth Rock (WPR) strains have been known to carry the sex-linked gene, and individuals carrying the gene may be identified by mating to red New Hampshires (NH) and pedigreeing to ascertain the down color and juvenile plumage color of offspring from individual males an females.

TESTING

A line pure for the sex-linked silver gene, S, may be easily synthesized by identifying males that are homozygous for the silver gene. These males will throw all white/yellow or all Columbian pattern (black on the head and around the eye and black primary flight feathers in the wing) day old chicks in mating with red (RNM) females.

| SILVER MALE<br>Ii Cc ee Ss | X<br>↓ | RED FEMALE<br>ii CC ee s– |
|---|---|---|
| MALE OFFSPRING<br>Ii Cc ee Ss or ii Cc ee Ss<br>White Columbian | | FEMALE OFFSPRING<br>Ii Cc ee S– or ii Cc ee S–<br>White Columbian |

These which are checked and identified pure for silver males, may then be mated to outstanding females of any commercial female line and F1 generation females will all be pure for silver

| CHECKED MALES<br>Ii Cc ee SS | X<br>↓ | OUTSTANDING COMMERCIAL FEMALES<br>ii Cc ee |
|---|---|---|
| | | FEMALE OFFSPRING<br>Ii Cc ee S–, ii Cc ee S–,<br>Ii CC ee S– or ii CC ee S–<br>Females all pure for silver |

The F1 generation silver females may then be mated to a similar set of checked silver males from another generation or source, and all the offspring males and females will be pure for silver.

However, some of the males will be carrying, I, C and E and these can be identified because they will not produce 100% Columbian pattern chicks. These males should not be used as first choice males for reproduction because the ultimate goal is to have the line homozygous, ii cc ee. Progeny testing the male candidates for production of Columbian chicks is done each generation until 100% of the males are proving correct. At this point, the newly synthesized line be closed. No further test matings will be necessary. Selecting the outstanding males and females for reproducing the line, will produce the required sex-linked silver line suitable for auto-sexing. All offspring of both sexes will be pure for silver gene, S, and the silver female line will have been produced.

Thus, for anyone skilled in the current art of poultry breeding, the synthesis of 1) a male parent gold line with fade-out genes, and 2) a female parent sex-linked silver line pure of silver, S- may be accomplished quite readily from carefully chosen stocks and deliberate work.

There should be no hidden problems, and the objective should be quite easily accomplished.

A. Development of Male Parent Line with Fade Out Genes Utilizing Peterson Commercial Lines

| YEARS | BREEDING STEPS |
|---|---|
| | STEP A |
| 1940–'43 | Obtain samples of best available purebred Red Cornish (RC) such as those in Northwest Arkansas. Obtain commercial samples of outstanding White Plymouth Rock (WPR) and White Cornish (WC) such as those from Dr. J. N. Thompson of Russellville, Arkansas. The best individual males and females of RC, WC, WPR were intermingled and allowed to mate at random. |

-continued

| YEARS | BREEDING STEPS |
|---|---|
| | Approximately 1000 day old chicks from 100,000 were placed from these matings. They were handled individually at 10 weeks of age and as adults selected according to body weight, body conformation and plumage color. |
| | The individual chickens that had the whitest undercoat of feathers, after the surface feathers were pushed aside, were most favored to be kept as breeders to reproduce the next generation. As adults, they were carefully examined for the presence of any black feathers or very dark red feathers, which automatically disqualified them as breeders. The general appearance of the chickens that were chosen as breeders was that described as White-Tailed Red (WTR) chicken, in which the outer feathers are light red and the undercoating of feathers of various sizes are creamy white. These selected parents were intermingled and mated at random. |
| 1944–'54 | Each generation about 1,000 day old chicks was hatched from the selected WTR parents and they were handled individually at 10 weeks age and as adults were selected as previously described. |
| | Since the flocks was closed to introduction of other chickens, it was deemed important to hatch at least 1,000 day old chicks per generation in order to minimize the inevitable effects of inbreeding that ultimately occurs in a closed population. |
| 1955 | An outstanding strain of meat-type male parent line of chickens was produced for breeding procedures from 1940–1955. This commercial Peterson strain was designated Line A. The chickens were of a beautiful white-tailed red plumage, but of somewhat lighter color than orthodox white-tailed red chickens, and as they were so distinctive, they were called the Peterson Paliminos by Dr. Don Warren, geneticist from Kansas and the USDA. |
| | The only problem with these chickens was that they were so heavily fleshed and short-legged that they had difficulty in mating, and the fertility in mating was lower than desired. |
| | STEP B |
| | In order to correct the low fertility of the Line A, a mild outcross was made to a strain of purebred New Hampshire (NH). Males of Line A were mated to New Hampshire females. |
| | STEP C |
| | The $F_1$ generation (first generation) chickens were mated back to Line A chickens, and the resulting progeny were closed as a new line H Peterson. |
| | New Line H Peterson chickens hatched as yellowish white down color with varying amounts of buff or light red markings on the head, neck and body. As adults, they were for the majority the typical White-Tailed Red (WTR) chickens, in which the overcoating of feathers are red, but some of the main tail, neck and wing feathers are white, particularly at the distal portion of the feathers. |
| | STEP D |
| | However, a startling and novel quality of the plumage of a minority of these chickens was observed. These chickens had a yellow-white down with reddish markings on the head and neck. As the juvenile feathers emerged, they were seen to be white with very little overcoating of red. At broiler age, these chickens gave very clean-looking dressed carcasses with no unsightly red "pin feathers". This interesting occurrence is more than likely due to genetic differences from the other contemporary chickens. The genotype of the typical White-Tailed Red H-line chickens was considered to be II CC ee s(s) . The genetic segregants that caused a bleaching out of red to all white feathers at broiler age would have to be at the E locus. The best candidate allelic gene at that locus to cause this novel effect would be the E birchen gene $E^R$. Therefore, the genotype of these new H-line chickens that bleach out from red to white plumage at broiler age may be designated II CC $E^RE^R$ s(s). This genotype II CC $E^RE^R$ s(s) may include multiple pairs of red feather modifying dilution genes. |
| | STEP E–K |
| | These new H-line segregant chickens are improved for growth rate and breast fleshing by crossing and back crossing to Line A Peterson and Line Z Peterson and Line Q Peterson, all of which are superior and commercially competitive to male parent lines in growth rate and fleshing. |
| | Crossing and back crossing improves growth rate and fleshing and maintains the red "fade-out" genes. SUPERIOR A MALES × H SEGREGANT FEMALES. |
| | The next step is to take $F_1$ generation HA females × H segregant males and close this line to future outside blood and select yellow white chicks with red markings on head to maintain the "fade-out" genotype. Repeat for at least 5 generations to fix body type and performance. |
| | Cross superior Z males × H segregant females = $F_1$ generation<br>$F_1$ generation = ZH females × H segregant males |
| | Close $F_2$ generation to further introduction of out side blood and select yellow chicks with red markings on head to maintain the "fade out" genotype. Repeat for at least 5 generations until body type and performance are fixed. |
| | Line Q × ZHA fixed × HA fixed. Take the Q line and select day-old chicks for distinct markings of red or brown on top of head and face. |
| | Line Q was developed over a period of 3 to 5 years from selecting out of the H line those minority of chicks that were reddish in down color, but as they became juveniles, the red color started to become dilute and as adults the feathers were entirely white. Of the 1,000 chicks, about 25 were selected each generation and mated among themselves and designated Q line to establish a distinction from all other lines. This is done to increase the frequency of the "fade-out" genes in this pure line so that it will be commercially competitive in growth rate and body conformation. |

B. Development of Silver Female Parent Line that will Auto-Sex Mate to Male Parent Line with the "Fade Out" Genes Utilizing Peterson Commercial Lines

| YEARS | BREEDING |
|---|---|
| | STEP A |
| 1957–Present | Silver White Wyndotte chicks were purchased from Canada. They were grown to broiler age and weighed and handled individually. The top 20% on growth rate and body conformation were grown to maturity. The best adult males were mated to outstanding individual Peterson White Plymouth Rock females. |

-continued

| YEARS | BREEDING |
|---|---|
| | STEP B |
| | The $F_1$ generation females were considered to be pure for silver and the males were regarded as heterozygous for silver.<br>The best $F_1$ individuals were mated among themselves to produce the $F_2$ generation. |
| | STEP C |
| | $F_2$ generation<br>males one-half pure for silver<br>one-half not pure for silver<br>females one-half silver<br>one-half gold<br>In this generation, the $F_2$ males were individually test mated to Red V-line (RV) Peterson females. RV females are a standard pure bred commercial line of red feathered chickens, which are used as test line to determine if chickens of other lines may carry the large S or silver gene. For example, a white male chicken that is pure for silver SS mated to a RV-line female, would produce all white feathered offspring because the silver gene S obliterates red color. Those males that sired all baby chicks that were silver or Columbia pattern (similar to silver), were identified as pure for silver.<br>These checked silver males were mated to the best females of that generation. The $F_3$ generation females were all known to be pure for silver. The $F_3$ generation males were test mated, and those pure for silver were mated to the silver females. |
| | STEP D |
| | The $F_4$ males and females were mated and would all be pure for silver, and no further testing was required. This line was closed to any further introduction of outside blood. It was established as a silver female line and improved for growth rate to broiler age, good egg production qualities, fertility, hatchability and liveability. This line is available for the dual purpose of producing:<br>(a) orthodox all white plumaged unsexed broilers when mated to orthodox males of any commercial male parent line, OR<br>(b) mating to a Peterson "fade out" gold male line to produce auto-sexed broilers at day of age. |

OBSERVATIONS AND PROCEDURES

It has been observed that selecting a female parent line of chickens with good early growth rate, good egg production, fertility, hatchability and liveability which carries the sex-linked dominant silver gene (S), assures that when the female parents are mated to males of this novel male parent line identified above, the male chicks inherit the dominant sex-linked silver gene which eliminates all colored red markings. The day-old male chicks have yellow-white down and white juvenile feathers and have substantially all white plumage as broilers. The male and female genotype produced broiler genotype as follows;

| Parents | Males | | Females |
|---|---|---|---|
| | II CC $E^RE^R$ ss | X | ii cc ee S__ |
| | | ↓ | |
| Broilers | Ii Cc $E^Re$ Ss | | Ii Cc $E^R$ e s__ |

It is to be noted that the male parent having multiple pairs of modifying dilution of red or red bleached out genes, will transmit one-half of those genes to male and female offspring alike, but will in fact show their activity in conjunction with the dominant birchen gene ER to cause a "fade out" of all red color in the feathers of the female broilers effectively culminating in all white plumaged female broilers at marketing and processing, thereby producing clean de-feathered eviscerated grade A carcasses devoid of any unsightly pin-feathers.

It is important to improve the two parent lines referred to above to increase their ability to yield offspring that will auto-sex with greater precision and frequency. Such improvement has always been found necessary in breeding stocks and is normally ongoing in reproducing the male parent line by recurrent selection for males that upon test-mating with females of the female parent line yield more obvious contrast in down color between male and female day-old chicks, thereby yielding ever-increasing accuracy in auto-sexing. The female parent line will be notably improved by assuring purity for the sex-linked silver gene by reproducing a female line only from males test mated with purebred red plumaged test females. Those males that produced all offspring that are all-white in down color will be considered pure or homozygous for the sex-linked silver gene SS.

The invention relates to a novel way of producing greater efficiency in broiler production by a new genetic approach at the primary broiler breeding farm. The new approach is to fabricate a novel gold male parent line as noted above, and a silver female parent line (carries the sex-linked silver gene. The gold and male line developed above is unique in that when mated to females of the silver lines, the day-old chicks maybe auto-sexed by color of the down and males and females placed and grown out in separate houses, thereby bringing for the producer the advantages of growing the sexes separately with no costs for determining the sex of the day-old chicks and no hindrance from production of female broilers with red feathers. The male day-old chicks are yellow-white and the females are reddish or buff, but during the growth to broiler age the females change feather color from red to white and do not leave any unsightly red "pin-feather" on the dressed carcass. The invention is unique in that an organization, producer, company, or farmer not desiring to auto-sex but to grow the sexes separately, may mate the same silver female parent line to any orthodox male parent line for the production of unsexed broilers (male and female all with white plumage as is the current practice in commercial broiler production). These explains in some details what has been previously stated in the earlier disclosure.

While this invention has been described as preferred, it is understood that it is capable of further modification, uses and/or adaptions following in general the principal of the invention and including such departures from the present disclosure as come within known or customary practice in the art to which the invention pertains, and as may be applied to the essential features set forth, and fall within the scope of the invention or the limits of the appended claims.

Having thus described my invention, what I claim is:

1. A method of producing hybrid chickens which can be color auto-sexed at day old and have fade-out plumage on females at broiler age comprising:

a) mating a male genotype II CC $E^R$ $E^R$ ss with modifying fade-out genes with a female genotype ii cc ee S__, whereby the resulting day old male chicks (Ii Cc $E^R$ e Ss) have white down and the resulting day old female chicks (Ii Cc $E^R$ e s__) have a buff or reddish colored down which will have faded out to become white plumage by the time the female chickens reach broiler age.

2. A method for color sexing chicks produced by the method of claim 1, comprising:

a) color auto-sexing said one day old chicks by optical observation; and b) separating buff or reddish colored female chicks from white colored male chicks.

3. The method of claim 2 and wherein:

a) said optical observation is by human observation of the overall appearance of said chicks.

4. The method of claim 2, wherein:

a) said optical observation is by electronic photocell sensing of the overall appearance of said chicks.

5. A male chicken having a fade-out genotype comprising II CC $E^R$ $E^R$ ss including modifying fade-out genes which when mated to a female chicken of genotype ii cc ee S- produces male progeny having white down at day old and female progeny having buff or reddish colored down at day old which will fade out to become white plumages at broiler age.

6. A female chicken of genotype ii cc ee S__ which when mated to a male chicken with a fade-out genotype II CC $E^R$ $E^R$ ss including modifying fade-out genes produces male progeny having white down at day old and female progeny having buff or reddish colored down at day old which will fade out to become white plumage at broiler age.

7. A silver female parent line of chickens for use in the production of marketable dressed, eviscerated carcasses, wherein:

a) females of said line of chickens have the genotype ii cc ee S__;

b) said line of chickens was derived from a breed selected from the group consisting of SWW, WPR and SX., c) said line of chickens was further selected over a series of successive generations for growth rate to broiler age, good egg production, fertility, hatchability and livability;

d) said line of chickens is genetically complementary to a male parent line having genotype II CC $E^R$ $E^R$ s(s) including modifying fade-out genes, whereby when a female of the female parent line is mated with a male of the male parent line auto-sexing broiler offspring are produced, the broiler male offspring having yellow-white down color at day-old age and the broiler female offspring having buff-reddish down color at day-old age; and e) said broiler female offspring upon reaching broiler age will have had said buff-reddish down color bleached out and become substantially all white, thereby eliminating the possibility of dark pin feathers on the dressed, eviscerated carcasses of said chickens.

8. A silver female parent line of chickens as in claim 7 and wherein:

a) said series of successive generations is at least five.

9. A silver female parent line of chickens as in claim 7 and wherein:

a) said female broiler offspring have reddish markings on head, wings and neck at broiler age.

10. An $F_1$ hybrid male chicken with genotype Ii Cc $E^R$e Ss and having white down at day old resulting from the mating of a male chicken of genotype II CC $E^R$ $E^R$ ss including modifying fade-out genes with a female chicken of genotype ii cc ee S__.

11. An $F_1$ hybrid female chicken of genotype Ii Cc $E^R$e s__ and having a buff or reddish color down at day old which will fade-out to become white plumage by the time the female chicken reaches broiler age resulting from the mating of a male chicken of genotype II CC $E^R$ $E^R$ ss including modifying fade-out genes with a female genotype ii cc ee S__.

* * * * *